United States Patent [19]

Guruswamy

[11] Patent Number: 4,762,594

[45] Date of Patent: Aug. 9, 1988

[54] APPARATUS AND METHODS FOR SENSING FLUID COMPONENTS

[75] Inventor: Vinodhini Guruswamy, Bethesda, Md.

[73] Assignee: MedTest Systems, Inc., Bethesda, Md.

[21] Appl. No.: 8,554

[22] Filed: Jan. 29, 1987

[51] Int. Cl.$^4$ ............................................. G01N 27/26
[52] U.S. Cl. ..................................... 204/1 T; 204/416
[58] Field of Search ............... 204/1 T, 416, 417, 418, 204/419

[56] References Cited

U.S. PATENT DOCUMENTS

| | | | |
|---|---|---|---|
| 3,413,199 | 11/1968 | Morrow | 204/1 B |
| 3,572,400 | 3/1971 | Casner et al. | 141/1 |
| 3,629,089 | 12/1971 | Luck | 204/412 |
| 4,214,968 | 7/1980 | Battaglia et al. | 204/418 |
| 4,233,031 | 11/1980 | Matson et al. | 204/412 |
| 4,272,245 | 6/1981 | Diamond et al. | 436/68 |
| 4,336,121 | 6/1982 | Enzer et al. | 204/403 |
| 4,340,457 | 7/1982 | Kater | 204/415 |
| 4,397,725 | 8/1983 | Enzer et al. | 204/1 T |
| 4,431,508 | 2/1984 | Brown, Jr. et al. | 204/418 |
| 4,549,951 | 10/1985 | Knudson et al. | 204/418 |
| 4,568,445 | 2/1986 | Cates et al. | 204/418 |

FOREIGN PATENT DOCUMENTS

0099745 6/1983 Japan ..................................... 204/416

Primary Examiner—John F. Niebling
Assistant Examiner—Steven P. Marquis
Attorney, Agent, or Firm—Hall, Myers & Rose

[57] ABSTRACT

Provided herein is a method for accurate, reproducible analytical solution evaluation eliminating the need for a reference sensor by determining the activity of selected species employing species specific sensors and species combination sensors in conjunction with Nernst-type equations. Also provided are sensor structures for elimination of edge effects to signals thereby yielding accurate, reproducible measurements, and a cartridge structure adapted to incorporate an array of the new sensors for employment of the new method where the cartridge is particularly adapted for miniaturization, maintaining a fixed volume of solution for analysis and providing an anaerobic testing environment. Lastly, a compact instrument embodying miniaturization especially adapted for field use and use of the cartridge is provided herein.

13 Claims, 3 Drawing Sheets

FLUX DENSITY PROFILE

DISTANCE FROM ELECTRODE CENTER

APPARATUS AND METHODS FOR SENSING FLUID COMPONENTS

TECHNICAL FIELD

This invention relates to analytical measurement of solutions and, particularly, to a method for reference-less sensor measurement employing single point calibration, a new electrode promoting uniform flux distribution, a new fixed volume anaerobic sensor cartridge and a new miniaturized instrument for analytical chemical measurements.

BACKGROUND OF THE INVENTION

The traditional "wet" chemistry techniques in analytical chemistry and its more sophisticated progeny, clinical chemistry, have in recent decades been replaced by electronic instrumentation. With the advent of instrumentaton, accuracy in reproducibility of experimental measurements has been enhanced. Such accuracy is of particular importance in clinical chemical techniques and of the greatest importance in biomedical measurements where minute (part per million) measurements are common. Linking such instrumentation and automated processing with the microprocessors and affordable computer technology, has resulted in another step in the evolution of analytical and clinical chemical techniques.

In the sub-discipline of electro-chemical measurements, great advances in such instrumentation have been made. Generally, conventional electro-chemical measurements require the measurement of two sample solutions containing two different known concentrations of a substance for calibration purposes followed by measurement of a solution containing an unknown quantity of the species. Electro-chemical methods generally require use of a reference electrode, a substance specific electrode and a bridge between the solution in order to achieve a cell for potentiometric measurements. The electrical signal (commonly in millivolts) obtained from the cell is proportional to the ionic activity and, therefore, concentration of the substance in the solution. The signal/concentration relationship is algebraically expressible by a Nernst equation $$V = M_f[C] + I + J \tag{1}$$

where
V is the voltage (signal)
$M_f$ is the slope (a constant for the particular electrode and substance)
I is a constant for a particular substance
J is the junction potential of the cell
[C] is the ionic activity (concentration of the substance).

In order to establish the values necessary to solve the equation, it is first required to determine the slope, $M_f$, for the electrode. For this step, measurement of two solutions containing known concentrations are taken, the values inputted into the above equation and the equations solved simultaneously to obtain the slope. Next, it is necessary to determine the constant, I, for the particular substance in solution relative to the particular electrode. The junction potential is also determined by conventional methods. The foregoing techhique is commonly referred to as a double or dual point calibration. Recent developments in electrode technology have dispensed with the need for the slope determination by providing preset, one-shot electrodes where the slope is known for a particular substance and electrode structure. These devices are generally limited, however, to one time use due to the slope shift after a period of exposure to solution. Slope shift is attributable to, among other causes, hydration of a previously unhydrated electrode. In view of this arrangement, such one shot electrodes are confined to use with specific systems and particular electrode arrangements.

Great improvements have been made in the sensitivity of sensors employed for electro-chemical analysis. Many relatively new sensor types have now found their way into the laboratory. Most notable are variants of the ion selective electrode (ISE), the enzyme base selective electrode (EBSE), the anti-body based selective electrode (ABSE), chemical field effect transducer (CHEMFET) and the ion selective field effect transducer (ISFET). Each of these sensor types may be incorporated into a number of physical variants including coated wire electrodes, thin film electrodes, etc. These are employable, not only for clinical chemical application, but also for general use in such fields as industrial chemical, pharmaceutical, biochemical, enviromental control, etc. Moreover, these devices now provide the technician with a considerable selection of devices and techniques which function to produce electrical signals proportional to the ionic activity of a particular substance or substances for which the sensors are specifically designed and, therefore, increasingly precise measurements.

Referring briefly to optical sensors and analytical methods primarily relying on colorometry, they, too, have experienced a corresponding rapid evolution. Significant advances are pronounced in the biochemistry field, e.g. enzyme and antibody-antigen reactions.

However, the technician is now faced with an increasing array of problems associated with the new technologies. For example, due to the sensitivity of the above-mentioned sensors, they may possess a bulky design. Notably, electro-chemical sensor systems generally require a reference electrode and species sensitive electrode, both of which must be carefully calibrated or preconditioned. Also, especially in the case of reference electrodes, supposedly identical electrodes may differ slightly due to manufacturing tolerances which can lead to erratic measurements, "drift" problems and junction potential errors.

Measurement variations may occur from use of such electrodes due to signal drift and varying junction potentials between the reference electrode in the media being studied and the associated electrodes. Junction potential contribution to the signal not only results from electrode structure, but also varies from instrument to instrument as well as measurement to measurement. For sensitive measurements, such variations are wholly unacceptable. Further problems are augmented by increasing sensitivity of the electrodes, particularly in biomedical applications, where precise measurements are critical. Factors such as the longevity, stability and contamination of the reference electrode, particularly when employed in hostile environments such as invasive monitoring during surgical procedures, must be accounted for, and have, thus far, escaped resolution. Finally, in devices requiring the relatively bulky reference electrode, electro-chemical systems have, for the most part, belied miniaturization.

During electro-chemical measurements of complex solutions (multicomponent) another problem arises, namely, separation of the signal from reference electrode junction potential. For measurement of complex solutions containing many potentially interactive electroactive species, in contrast to elementary assessment of a single species solution, the coefficient of activity (contribution by individual components) will defy precise determination due to electro-chemical synergy. Hence, the electro-chemical measurements of complex organic solutions, such as blood, necessitate interpretation of the signal due to the lack of precision in identifying the contribution of a particular targeted substance. Where precise measurements are required, the ambiguity stemming from such interpretation is, at best, risky and, at worst, lethal. Moreover, the contribution of drift by both the reference electrode and the specimen electrode coupled with the junction potential identification problem, could lead to anomalous measurements.

Moving now to a practical problem associated with prior art systems, it is the manufacture and supply of both species specific electrodes and reference electrodes. Generally, the reference electrodes are of a more sophisticated construction in order that they be reusable. Without more, it is evident that measurements using such electrodes would differ in every instance due to manufacturing tolerances. Accordingly, not only are the drift and calibration problems extant, but, also, standardization is difficult especially when conducting the several measurements of different solutions required for calibration and unknown solution evaluation.

Most analytical systems are exposed to the ambient environment. They are not anaerobic. An anaerobic environment is desirable, first, to more closely match in vivo conditions. Furthermore, it is important, for example, in blood gas analysis to avoid sample contamination from air so as to avoid skewing the results. Lastly, to obtain a series of substance measurements from a sample, requires considerable time and many individual measurements. Not only is the time factor detrimental but, also, specimen contamination and chemical changes in the specimen are likely to occur. Hence, it is desirable to maintain an anaerobic measuring environment to achieve accurate measurements of certain substances, and most notably, blood gas concentrations. Lastly, most known systems do not contemplate fixing or providing fixed volume delivery. Elaborate stirring or mixing arrangements are used to insure uniform transport to the sensor. It would be desirable to conduct measurements of a fixed volume of solution and especially desirable to provide analysis requiring only a small volume of solution uniformly delivered to the sensor to make the measurements.

Other practical considerations arise relative to laboratory use by the clinician. In the event that a system is intended to be reusable, it is incumbent upon the operator or technician to insure that the electrodes are not contaminated when preparing for a test. Thorough cleaning and recalibration is necessary for each use. Such efforts require considerable labor and render cost ineffective the use of reusable systems especially in hospital laboratories, etc. Where disposable systems are employed, problems arise relating to the technician's techniques.

Another aspect of electro-chemical apparatus that has escaped development is a compact, simply employable, field or laboratory use instrument which can be operated by persons having a minimum of skilled training. Miniaturized and standardized equipments are not available for providing analytical electro-chemical measurements like those described above.

SUMMARY OF THE INVENTION

It is, therefore, an object of this invention to overcome the problems experienced with the use of prior art techniques and methods.

It is another object of this invention to provide a method for generating accurate and reproducible substance concentration measurements.

Still another object of this invention is to provide a method and apparatus for electro-chemical measurement requiring single point calibration for potentiometric, potentiostatic or resistivity analysis.

Still another object of this invention is to provide method and apparatus for electro-chemical substance concentration determinations with a minimum cost and a minimum of effort by eliminating the requirement for a reference electrode.

It is another object of this invention to measure true activities of targeted species in biological solutions without interference from junction potential errors caused by a reference electrode.

Yet another object of this invention is to provide techniques and apparatus for speedy measurements to avoid time-dependent internal changes, to maximize stability and to minimize potential contamination of the sensors.

It is another object of this invention to provide techniques and apparatus minimizing potential technician error and avoiding the need for technician interpretation.

Still another object of this invention is to provide apparatus for solution analysis which maintains the solution in an anaerobic environment.

Another object of this invention is to provide delivery of a fixed volume of solutions for measurement.

Still another object of this invention is to provide measuring methods and apparatus equally applicable to a range of analytical purposes such as electro-chemical and optical measurements.

Yet another object of this invention is to provide techniques and apparatus capable of miniaturization and which is capable of employing an array of sensors for real-time, multispecies solution analysis.

Another object of this invention is to provide a cartridge which is disposable or capable of reuse.

A further object of this invention is to provide a modular cartridge system where different cartridges for different measurements may be sequentially introduced to signal processing apparatus.

It is another object of this invention to provide a universal sensor cartridge capable of incorporating a large number of different sensors for a broad range of different analytical techniques.

These and other objects are satisfied in part by a method for single point calibration measurement of at least a first and a second species in solution employing at least a first, second and third sensors where the first sensor is sensitive to the first and second species, the second sensor is sensitive to the first species and the third sensor is sensitive to the second species. The method contemplates contacting the sensors with a solution containing the first and second species, obtaining first and second signals where the first signal is the difference between said first and second sensors and said second signal is the difference between said first and third sensors. The signals are then conveyed to a signal processor. The next step involves contacting the sensors with a second solution containing known quantities of the first and second species and obtaining third and fourth signals from the first and second sensors and said first and third sensors, respectively, which are conveyed to a signal processor, establishing algebraic constants from said third and fourth signals, inputting the constants into a calculating device determining the concentration of said first and second species. Equivalently, the technique can be performed by first introducing the known solution and the unknown solution subsequently. Also, as should be apparent to the skilled artisan, the concentration determination is the equivalent of determining the activity of the particular substances in solution. Summarizing the benefits provided by this technique, in electro-chemical procedures, it eliminates the need for a reference electrode and corresponding slope and intercept variations. It is readily adaptable to miniaturization. It requires only comparative measurements between determined species and only N+1 sensors for measurement of N species. Moreover, it minimizes labor and interpretation errors, especially when combined with equipments described herein.

Still other objects of this invention are satisfied by a cartridge for facilitating analytical measurement of a solution, comprising a housing and a chamber for containing a predefined volume of solution, the chamber having a first end and a second end and being disposed within the housing. Combined with the chamber are an inlet port in fluid communication therewith which is located proximate to said first chamber end, and a waste reservoir of preselected volume in fluid communication with the chamber. Within the chamber is a means for minimizing fluid back-flow from said reservoir to said chamber and a sensor element disposed in the housing and interfacing with the chamber at a preselected location between the first end and the back-flow minimizing means. Lastly, the cartridge has a means for conveying signals generated by the sensor through and out of the housing.

This cartridge is preferably constructed for a miniaturized instrument, maintains the test solution in an anaerobic environment, requires introduction of only a small amount of solution for test procedures, is adapted for incorporation of a number of different sensors and sensor types and even contemplates disposability.

Still further objects of this invention are satisfied by providing a sensor for evaluating a species in solution. The sensor embodies a conductive element capable of conducting signals having a first surface of particular cross-sectional dimensions coupled with species specific reactive means for reacting with a selected active species in solution. The reactive means is in intimate contact with the conductive element and capable of generating a signal corresponding to the active species in solution. The reactive means is sized to cover the first surface and extend a substantial distance beyond the perimeter of the first surface to minimize edge effects.

The sensor arrangement, stated positively, facilitates uniform and reproducible measurements of a solution by insuring uniform interaction between the species specific receptor and the signal conductor at the interface of the receptor and conductor. This is accomplished by eliminating or minimizing edge effects at the conductor perimeter. The sensor is contemplated for incorporation in the equipments described herein and is readily adapted for use with the referenceless technique. The critical teaching of the sensor structure is contrary to popular belief. That is, it is not a precise sensor geometry which provides uniform measurement particularly for single point calibration procedures but the provision of a substantial overlap that minimizes edge effect contributions and enhances measurements of greater precision irrespective of the sensor geometry.

Certain of the objects stated above are finally satisfied by a compact instrument for solution analysis. The instrument includes a housing, an information display means contained on a surface of the housing for displaying information, selection means for selecting the information to be displayed, a receptacle of predetermined dimensions positioned on the housing, and means for processing electrical signals and conveying the processed signals to the information display. The instrument further includes a sensor containing cartridge for sensing properties of a solution and generating signals corresponding to the sensed properties. The cartridge is dimensioned to fit in said receptacle.

The described instrument is of a nature to provide a far simpler, miniaturized, easily handled analytical tool especially suited for field use. It contemplates minimizing the degree of clinical skill, knowledge and labor required to operate and obtain accurate solution analysis. When combined with the methods and apparatus described herein, the instrument is especially suited to provide a wide variety of analytical determinations employing a host of different sensors and sensor types to achieve rapid sample evaluations.

In summary, the present invention provides a new referenceless analytical method, a new sensor structure eliminating contribution from edge effects, a cartridge which, among other aspects, is adapted for miniaturization and maintaining the test solution in a neutral environment, and a compact, self-contained, readily-employed analytical measurement processing unit.

Given the foregoing summary, the skilled artisan will more readily appreciate the advance this invention provides from review of the following detailed description of the illustrated embodiments.

DETAILED DESCRIPTION OF THE ILLUSTRATED EMBODIMENTS

For organizational purposes, the illustrated embodiments will be described first by the new method in the context of electro-chemical analysis of specified substrates; secondly, by the sensor structure in the form of an electrode; thirdly, by a sensor assembly in the form of a miniaturized electrode containing cartridge; and lastly, a miniaturized microprocessor based and solar powered instrument for field or laboratory use.

At the outset, it should be noted that the illustrated embodiments contemplate precise structures and miniaturization which are not necessary for practice of certain aspects of the invention. For example, it is evident that laboratory equipment of considerable size can be constructed. Also, multiple purpose cartridges incorporating reference electrodes can be provided each which embodies certain concepts described herein. Accordingly, it is not intended that the invention be so limited to the specific recitation below.

THE METHOD

Figure 1:
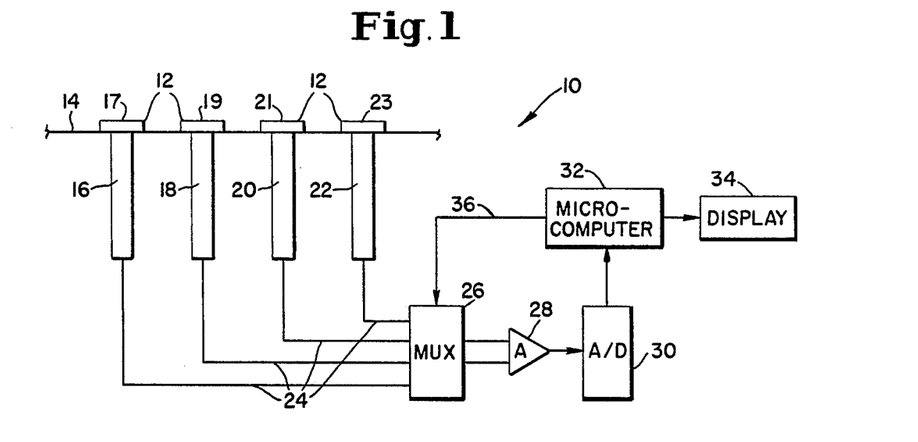
FIG. 1 is a schematic representation of a sensor arrangement of the invention.

Turning now to the method and referring to FIG. 1, it depicts multi-channel sensor system 10. Sensor 10 features an array of sensors 12 composed in this case of four individual electrode sensors, 16, 18, 20 and 22. For the purpose of illustrative simplicity, electroactive sensor 16 is deemed to be sensitive to a species A, sensor 18 is sensitive to a species B, sensor 20 is sensitive to species A and B, and sensor 22 is sensitive to species A and C. (These species may be chosen from many species such as potassium, sodium, chlorine, hydrogen ion, or selected biological and organic molecules.) All of species A, B and C are substances contained in a fluid which is to be electro-chemically evaluated using one of the two variations of the below-described method. More particularly, it is anticipated that a complex biological fluid such as blood will be subject to such an evaluation.

Although described in greater detail below, species specific covering membranes 17, 19, 21, and 23, corresponding respectively to sensors 16, 18, 20 and 22, are impregnated with ion selected materials where the electrodes are sensitive to A, B and C and combinations A and B as well as A and C, respectively. The membranes and sensors are so arranged to provide for a substantially uniform electrical signal caused by interaction between the target species in solution and the electroactive compound in the membrane. A corresponding charge develops between the membrane and the sensor thereby generating a charge distribution and potential proportional to the ionic activity of the species.

The principal variant of the inventive technique is now described with reference to potentiometric electrode sensors 16, 18 and 20. It should be appreciated by the skilled artisan that sensors 16, 18 and 20 represent half-cells where the combination of two half-cells provide an electro-motive force (EMF), representative of the potential difference between each of the respective sensors. Turning first to sensor 20, it is a combination electrode for species A and B, its electrical potential, in simplest form, is expressed by the equation $$E_{20half} = M_A \log C_A + M_B \log C_B + I_{AB} \quad (2)$$

$M_A$ and $M_B$ are constants for species A and B, respectively, which for particular compositions and electrodes, can be predetermined and programmed into a calculation device. $C_A$ and $C_B$ are the concentrations of species A and species B, respectively. Equation 2 can be further reduced to the expression:

$$E_{20half} = M_{AB}[\log C_A + \log C_B] + I_{AB} \quad (3)$$

where the quantity of the electroactive species impregnate into membrane 21 is carefully proportioned. For each such combination, before manufacture, it would first be necessary to evaluate the amounts to establish the most effective combination to obtain the simpler equation.

Moving now to the other electrodes, the electrical potential of sensor 18 which is sensitive to species B is expressible by the equation $$E_{18half} = M_B \log[C_B] + I_B \quad (4)$$

Likewise, the half-cell potential of sensor 16 specific to species A is expressible as $$E_{16half} = M_A \log[C_A] + I_A \quad (5)$$

To one of ordinary skill in the art, the foregoing equations represent the classical Nernst-type equations obtained from ion selective electrodes for measurement against standard electrodes. The instant invention, however, eliminates the need for a reference electrode and its contribution to the signal. The elimination of the reference electrodes is accomplished by establishing cells between sensors 16 and 20 and sensors 18 and 20, conveying the signals over wires 24 to multiplexer 26 which is commanded over wires 36 by microcomputer 32. The signals are sent to op-amp 28; in this case a differential amplifier, where signals from 16 and 18 are passed to analog/digital converter 30 and, ultimately, to microcomputer 32 and display 34. The differential potentials corresponding to $E_{20}-E_{18}$ and $E_{20}-E_{16}$ are thus obtained. The differential signals are expressed by the equations $$E_{20-18} = (M_A \log[C_A] + M_B \log[C_B + I_{AB}]) - (M_B \log[C_B] + I_B) \quad (6)$$

Put more simply $$E_{20-18} = M_A \log[C_A] + I_{AB} - I_B \quad (7)$$

Correspondingly, $$E_{20-16} = M_B \log[C_B] + I_{AB} - I_A. \quad (8)$$

The slope values $M_A$, $M_B$, $M_{AB}$ and any other slope constants are known from prior testing of the particular electrode structures with standard solutions. These values are either inputted or stored in microcomputer 32 for inclusion into the equations. Therefore, with the slope values and the signal values known, the constants and the concentration values are determinable given measurement of a reference solution to determine the constants. In order to solve the equations, a reference solution having known concentrations of species A and B is measured. Since the constants $I_A$, $I_B$ and $I_{AB}$ are the same for both solutions, their contribution to the equation is subtracted out:

$$E_{20-18standard} - E_{20-18test} = M_A(\log[C_A]_{(standard)} - M_A \log[C_A]_{(test)} \quad (9)$$

Knowing the signal potential and the slope (M) values permits direct calculation of $C_A$ and $C_B$. By the foregoing, to obtain differential measurements of two distinct species requires only three electrodes; one electrode being selective for the combination of both species being tested and, then, two individual electrodes selected to each of the selected species being tested. Viewed simplistically, the combination electrode provides a signal corresponding to the activity of $A+B$ where if the contribution of species A is substracted from the signal, the concentration of B is determined. Correspondingly, where the contribution of species B subtracted from the combination electrode value, concentration of species A is determinable.

A second method for analysis of a greater number of species, can be practiced by the invention. Employing the foregoing principles, the concentration of a third species, C, may be determined by employing, at minimum, the fourth combination electrode 22 sensitive to species A and C. The concentration of C is determined by subtracting the signal produced by electrode 16 from electrode 22. In such a case the calibration solution must also include species C.

It should now be readily appreciated that the inventive method requires only one additional electrode to the number of species being evaluated. Mathematically, if N is the number of species targeted for analysis, only N+1 sensors are required to practice the technique. Moreover, the technique requires measurement of only two species containing solutions, the calibrant and the unknown solution.

A multiple combination system, as described above in the second embodiment, may exhibit some interference due to the presence of additional species (B) in solution. Accordingly, it may prove advantageous to have additional electrodes sensitive to species C alone or/and the combination of A, B and C. In such a case, the calculation apparatus are employed to provide comparative data between the species specific electrodes 16, 18 and 22 or the combination electrodes 20 and one sensitive to species A, B and C. Since multiple combination electrodes (more than two species) may be subject to electro-chemically synergistic interaction, anomalous signals may result. Hence, it is suggested that each electrode's sensitivity be limited to two species.

In summary, this invention permits evaluation of a solution for (N) separate species requiring only two measurements, the unknown solution and the calibrant solution, using only (N+1) electrodes.

Some aspects of the above-described technique should now be underscored. Principally, in the context of electro-chemical analysis, the method dispenses with the need for a reference electrode and, therefore, eliminates considerations for junction potential. Furthermore, elimination of the reference electrode minimizes "drift" problems by reducing the drift occurrence to two similarly structured electrodes. Rather than exhibiting relative combined drift of both the reference and species specific electrode each contributing its own district drift due to dissimilar geometries, compositions, etc., employing similarly structured and composed electrodes provides comparatively uniform drift. Hence, the drift component is often negligible or linear and assessable. It is not exponential and difficult to assess. (Drift is squared due to the separate contribution of reference and species electrodes.) Secondly, the method lends itself to use in miniaturized devices.

It should be evident to the skilled artisan that not only does the instant method provide a labor saving technique for multicomponent electro-chemical analysis but also is an expedient for rendering real-time results when needed. These benefits are especially important in a clinical chemical environment during sensitive procedures such as surgery on a human patient.

ELECTRODE STRUCTURE

Conventional electrodes may be used with foregoing techniques and in the below-described apparatus. For example, wire, wire coated, and film electrodes, thick or thin film electrodes of a redox, semiconductor or type involving a polymeric matrix immobilizing an electrochemically active receptor impregnated therein, can be used. More specifically, variants of the thin film electrode described in U.S. Pat. No. 4,214,968, the graphite electrode described in U.S. Pat. No. 4,431,508 and the convex-domed electrode described in U.S. Pat. No. 4,549,951, may all be employed in the arrangements and methods described herein and for that reason are incorporated by reference.

The modification of the foregoing electrodes involves the selection of the ion selective electrode portion or membrane having a substantially greater cross-sectional area than the underlying conductor in order to promote uniform charge density between the solution and the conductor.

It has been suggested previously (see U.S. Pat. No. 4,549,951) that a convex geometric configuration of the membrane contributed to promote uniformity of signals from transport of the electroactive species of an ion selective membrane to the interfacing cross-section of the conductor and, thus, accuracy and reproducibility of measurements. The dome-shaped membrane electrode was conceived of for this purpose. However, what went unrecognized is the contribution of edge effects to space charge distribution and transport phenomena and, hence, (adherence from surface tension, greater electron transfer, etc., generated along the perimeter of the conductive body) to the signal. Basically, edge effects result from nonuniform layers of charge distribution between the interfaces of solution, the membrane and the electrically conductive member of the electrode. The nonuniformity is particularly pronounced along the perimeter of the conductor and membrane due to surface phenomena and exposure to a relatively greater volume of solution with a corresponding higher density of flux. This factor gives rise to slope variations from electrode to electrode even for the same species.

It has now been found that the elimination of edge effects promotes signal uniformity without a need to restrict the configuration of the membrane to a particular geometry. Accordingly, it is now believed to be no need for the membrane to possess any particular geometric configuration (dome shape, etc.) but rather to provide an area of sufficiently greater size than the conductor cross-section to minimize edge effects. Indeed, it is preferred to provide a membrane surface area having at least approximately twice the size of the cross-sectional area of the conductor. However, more precisely, the degree of membrane overlap is mathematically accessible from the membrane/electrode geometry and classical electron transport equations.

Figure 2:
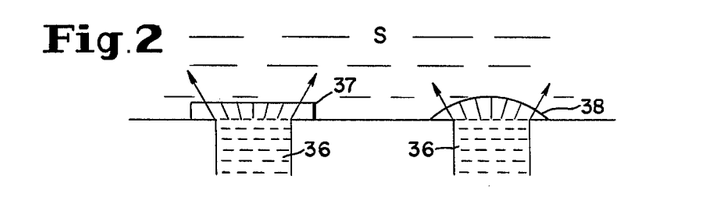
FIG. 2 is a graphical depiction of flux density distribution across sensors.

Referring briefly to FIG. 2, it graphically depicts the electron pathways between solution S, rectangularly cross-section membrane 37, and domed membrane 38 to underlying conductors 36. Although some signal contribution occurs from the outer membrane portions, the predominate uniform flux distribution is generated from the portion overlying the electrode and a bevelled portion of between 30° to 45° flaring from the edge of conductor 36. To promote uniformity of edge effect and, therefore, avoid nonuniform measurement, the membrane area is increased to extend well beyond the perimeter of the conductor.

Figure 7:
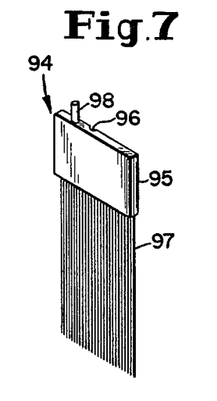
FIG. 7 is a perspective view of a disposable, sensor-containing cartridge.
Figure 8:
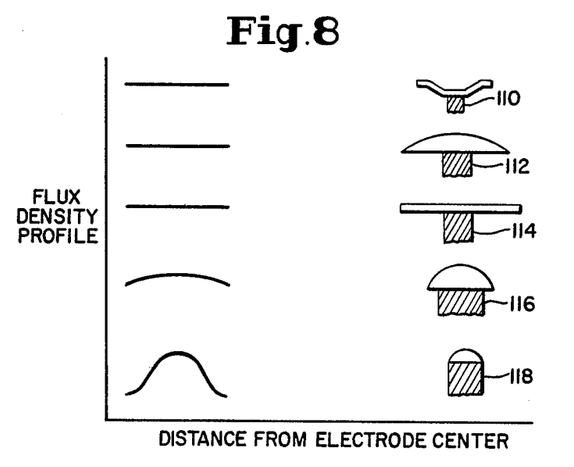
FIG. 8 is a graphical representation of the sensor construction and flux density variations caused by edge effects.

Turning briefly to FIG. 8, it represents the contribution of edge effects to various electrode structures. Electrodes 110, 112 and 114, having concave, convex and flat membranes, respectively, each demonstrate uniform flux density across the entire conductor surface. Convex domed electrode 116, having a membrane extending a little beyond the conductor perimeter, exhibits a small deviation in flux density. Electrode 118, with no extension exhibits considerable flux density variation across the conductor surface. As stated above, FIG. 7 underscores the fact that this invention contemplates the miniaturization of nonuniform flux density along the edge of the electrode by providing a membrane of considerably greater cross-section than the underlying conductor surface. Hence, the instant invention contemplates that the electrode will contain a species reactive portion or membrane having an overlap so as to possess a solution interface area considerably greater (approximately twice) than the cross-section of the conductor.

In summary, the electrodes contemplated for use in the instant invention are known electrodes modified to provide an increased electro-chemically active surface of considerably greater surface contact area than the underlying electrically conductive portion of the electrode to eliminate edge effects and corresponding uneven flux density.

THE CARTRIDGE

The contemplated sensor containing cartridge is intended to contain several microsensors of similar or different types, maintain an anaerobic sample chamber, and provide a fixed value delivery means to the fixed volume chamber.

Figure 3:
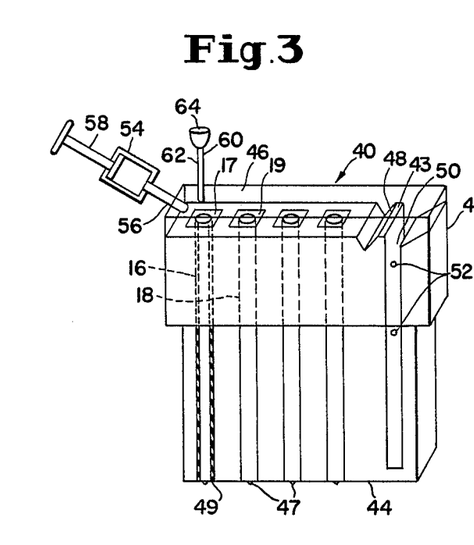
FIG. 3 is a perspective view of a sensor cartridge of the invention.

Referring now to FIG. 3, it depicts cartridge 40 comprising two principal sections, chamber housing 42 and lower insert portion 44. Contained within chamber housing 42 is fixed volume chamber 46 designed, typically, to hold a volume of less than one milliliter and preferably between 10-50 microliters. Chamber 46 is generally of a rectangular configuration and is sealed within chamber housing 42. Within chamber housing 42, sensors 16, 18, 20 and 22 are embedded and disposed in an array on the lower surface of chamber 46. The sensors are electrically isolated from each other and are positioned in chamber 46 in a manner where fluid introduced therein will completely cover membranes 17, 19, etc.

Disposed transversely along one side of chamber 46, is vented waste reservoir 50 having a volume capacity of 4-6 times that of chamber 46. One direction flow vents 52 are provided at selected locations in order for air or gas to escape and allow fluid from chamber 42 to evenly flow into and fill reservoir 50. Between reservoir 50 and the sensors are located furrow 48 and weir 43. Furrow 48 and weir 43 are designed to prevent fluid back-flow from waste reservoir 50 into chamber 46 having disposed on its lower surface the array of sensors. Especially where intended for use in the field, weir 43 should be of a height exceeding the thickness of membranes 17, 19, etc. to maintain the test solution thereover. Furrow 48 and weir 43 serve to prevent fluid back-flow from waste reservoir 50 into chamber 46 and resulting mass transfer and contamination between the waste fluids and the analytical fluid. It is noted that the weir may be unnecessary where the cartridge is of a design to take advantage of surface tension to stabilize the sample fluid, on the one hand, and the calibrant fluid, on the other hand, over the sensor.

At the opposite end of chamber housing 42 from waste reservoir 50 are calibration fluid input port 56, calibration fluid syringe 54 and specimen inlet port 62 with specimen input element 60 extending therefrom. Specimen input element 60 provides a rubber septum across its upper surface for injection of the specimen into element 60 through port 62 and into chamber 46 from a conventional syringe or, alternatively, a capillary tube. Although it is desirable to inject an amount of specimen fluid equal to the volume of chamber 46, any excess will flow into furrow 48 and, subsequently, into waste reservoir 50.

Calibration fluid syringe 54 contains a predetermined volume of an appropriate calibration fluid containing substances for which the sensors arrayed within chamber 46 are sensitive. Preferably, a controlled volume of calibration fluid is injected into chamber 46 by depressing plunger 58 where the fluid flows through input port 56 and into the chamber.

Moving now to the structure lower insert portion 44, like chamber housing 42, it is preferably composed of a suitably rigid, strong, transparent polymer having the conductive elements (graphite, wire, etc) from sensors 16, 18, etc., extending through its entire length.

By providing significant sensor elongation, especially when electro-chemical measurements are performed, the elongation minimizes signal interferences from adjacent sensors. As a practical matter, during manufacture of a membrane covered electrode, the membrane is deposited over the conductor in a partially gelled condition. The remaining solvent, generally organic, is then evaporated. However, some solvent will migrate into pores in the cartridge body. Migrating solvent can carry with it the electroactive species. Hence, the cartridge body, itself, may be sensitized or even cross-sensitized. Where electrodes are positioned very close to each other, cross-contamination can occur. Thus, a species specific electrode may generate a small signal corresponding to another species for which the neighboring electrode is sensitive. This possibility is enhanced when the cartridge body is very short, the degree of migration is correspondingly reduced, and intermingling occurs close to the sensor receptor surface. By elongating the sensors and cartridge, gravity causes the solution bearing, residual electroactive species to follow a downward path adjacent the electrode instead of transverse intermingling a short distance from the receptor membrane. Hence, it is preferred that the cartridge be of sufficient length to minimize such effects.

Returning to the structure of cartridge 40, waste reservoir 50 extends toward the bottom of lower insert portion 44. Projecting from the bottom of chamber 44 are electrical point contacts 47 which provide electrical communication between sensors 16, 18, and an appropriate signal detector. Due to potential internal signal interference or interference from external electrical noise, it may be desirable to insulate each of sensors 16, 18, etc. Accordingly, sensor 16 is illustrated with insulative sheathing 49 disposed therearound. If all the sensors are so insulated, the opportunity for electrical signal interference is minimized.

In brief, cartridge 40 is used by injecting a sufficient volume of the specimen fluid into chamber 46 via inlet port 62 to fill chamber 46. Measurements of the electrochemical activity are made via the array of sensors.

Once measurements are taken, a fixed volume of calibration fluid is introduced via syringe 54 through input port 56 which washes the specimen fluid from chamber 46 into furrow 48 over weir 43 and into waste reservoir 50. A second portion is added which washes the first portion out of chamber 46 over weir 43 and into reservoir 50. Finally, a third portion is added to displace the second portion. By this means, residual specimen fluid is substantially completely removed from chamber 46 and electro-chemically active membranes 17, 19, etc. Furthermore, by providing multiple washings, if the specimen contains a higher concentration of a particular ion than the calibration fluid, the multiple washings permit an equilibrium to be established to minimize inaccurate measurements of a particular ion concentration in the calibrant solution due to residual ionic activity from the specimen on membranes 17, 19, etc.

Figure 4:
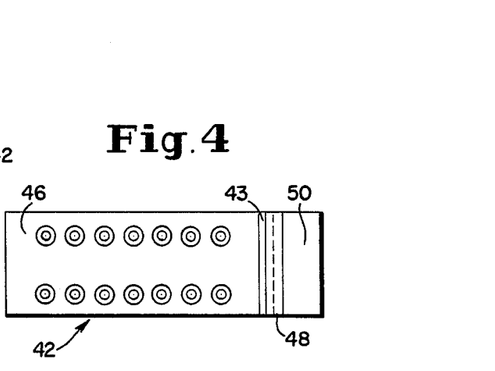
FIG. 4 is a top view of a sensor array.

In FIG. 4 is illustrated an alternative embodiment of cartridge chamber housing 42 and chamber 46. In this embodiment there is an array of fourteen sensors which have the capacity for analysis of as many as thirteen electro-chemical active species. At one end of chamber 46, like the embodiment in FIG. 3, is disposed waste reservoir 50 for containing the analyzed specimen sample and the volume of calibration fluid employed for washing out the specimen fluid from chamber 46. Between reservoir 50 and the array of sensors is disposed furrow 48 and weir 43. Weir 43 in this case is positioned between the furrow and the sensors and assists to define a specific volume of fluid that will be contained within chamber 46. The fluid introduction may follow the steps described above or, alternatively, the calibrant may first be introduced into chamber 46 and measurements taken followed by introduction of the specimen solution into the chamber with measurements being taken of the specimen fluid. Where the calibrant is first introduced, it is possible to eliminate particular washing steps by providing a relatively substantial volume of specimen fluid to displace the calibrant solution, develop an equilibrium and be subject to measurement. Any excess specimen fluid will flow into waste reservoir 50.

The above-described cartridge embodiments are contemplated as being disposable as they would be composed of a relatively, inexpensive polymeric material. However, it is also possible to reuse the cartridge, given the inclusion of reusable sensors within the cartridge, by properly cleaning and otherwise freeing cartridge 40 from contamination. As would be expected in such an embodiment, reservoir 50 would be provided with an appropriate fluid outlet near or at the bottom of the reservoir in lower insert portion 44 in order to permit a series of appropriate washings. Another alternative construction would be to provide an open-topped fluid containing chamber 46. This, in certain cases, would be undesirable as it would eliminate the anaerobic environment by exposing the species and calibrant to an ambient atmosphere. (As noted above, particularly in the context of biomedical measurements, it is preferred to maintain an anaerobic environment.) For this reason, it is suggested that chamber 46 and waste reservoir 50 be flushed with a neutral gas such as nitrogen following construction and prior to use to minimize the presence of atmospheric oxygen and carbon dioxide during testing.

An additional construction variant includes modifying element 60 to be a flow diversion valve or dispenser adapted to extract a sample directly from the source. For example, element 60 may be combined with a catheter to extract blood directly from a patient's body. Point contacts 47 may also be modified both in structure and position. They may exit lower portion 44 on its side and be of a structure to establish wiping electrical contact with an appropriate mating receptacle.

Lastly, it is possible to modify the cartridge for instruments other than electro-chemical analyzers. For example, optical fibers could be incorporated for measurement of fluid optical properties. In this case, it would be suggested to have source fibers and receptor fibers disposed in an array to maximize optical transmission and reception. Preferably, conventional available coaxial fibers would be used. Moreover, the upper surface of chamber 46 can be coated with an optically reflective material. An additional variant would be optical colorometric analysis of the covering membrane impregnated with a species specific interactive substance which undergoes a color change upon reaction. Color changes can be detected using coaxial optical sensors. As one further variant, optical and electrochemical sensors can be combined in the same cartridge.

In summary, cartridge 40 serves the function of positionally stabilizing and maintaining a specific geometry between the sensors housed therein, defines a precise volume of fluid for analysis, provides an anaerobic testing environment, avoids sensor contamination, provides waste contaminant while avoiding fluid intermingling and means for precise alignment of the sensors with appropriate detection apparatus. Moreover, it is adaptable for use with a host of conventional sensors, for example, potentiometric, potentiostatic, resistance, colorometric, etc., analysis.

MINIATURIZED SYSTE

Figure 5:
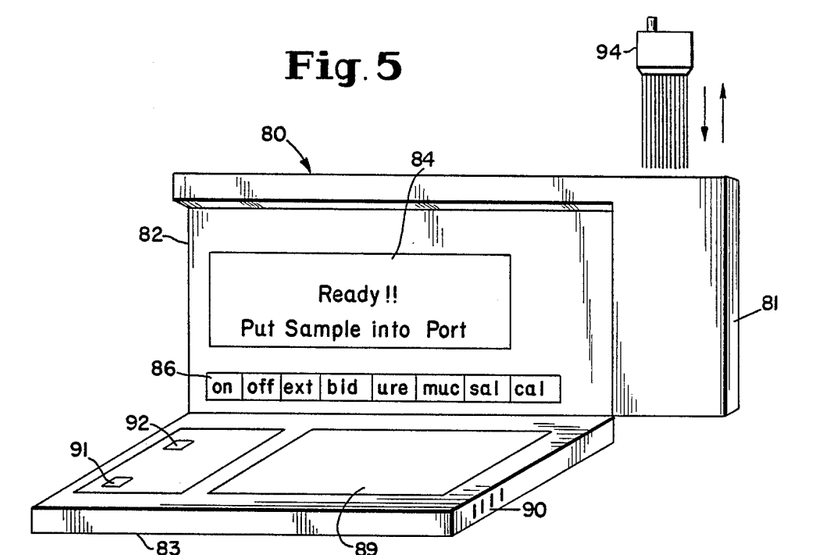
FIG. 5 is a perspective view of a compact instrument of the invention.
Figure 6:
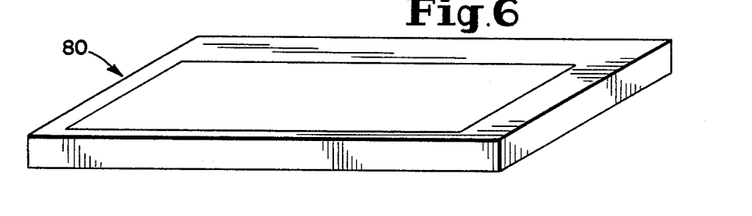
FIG. 6 is a view of the instrument in a folded configuration.

In FIGS. 5 and 6 are depicted a miniaturized instrument for use of a sensor containing cartridge, like that described above, containing electrodes, like those disclosed above, and contemplating measurements by the analytical techniques set forth above. Compact instrument 80 dedicated for biomedical use, is comprised of fold-up case 82 featuring upper portion 81 and fold-out portion 83 which are hinged (not shown). The electronic components employed within the case are commercially available. They are microprocessors, random access memories (RAM)s, read only memories (ROM)s, amplifiers, switches, analog to digital converters, power capacitors, transformers, etc.

The principal features of upper portion 81 are liquid crystal display panel 84, controlled by the microprocessor (not shown) and a row of actuation buttons 86 for activating the particular function desired. Upper portion 81 is also provided with an appropriately sized cartridge receptacle (not illustrated) to permit insertion of sensor cartridge 94 therein. Once inserted, as described above, the electrodes contained by cartridge 94 are processed and are displayable on the liquid crystal display screen. Buttons 86 facilitate selection of the desired, W for example, particular blood gas concentrations or even blood pressure, on display 84. The receptacle can be modified to include an optical character recognition device or magnetic pickup device for reading information placed on the side of cartridge 94. For example, a bar code or piece of magnetically encoded tape can be positioned on the cartridge which would automatically input data such as slope values (see method above), identify specific sensors and combination sensors, etc. The modification would eliminate the need for the operator to input such values and information by, for example, a programming keyboard (not illustrated). Furthermore, the codes could reprogram buttons 86 for specific tests performed by specific cartridges.

Lower panel 83 features a solar power panel 89, RS232 port 90 and plug-in adaptors 91 and 92 for connecting peripheral equipment such as a phonocardiogram and blood pressure monitor. Signals from a phonocardiogram or blood pressure monitor are displayable on the LCD following appropriate signal processing by the microprocessor and activation by the appropriate button. RS232 port 90 permits digital communication between the unit and a remote digitalized patient information storage area should it be desirable to convey the data processed from cartridge 94 or from ancillary equipment such as the above-stated phonocardiogram or blood pressure monitor to a computer, etc. Due to the advances in microprocessor and electronics technology, in addition to the miniaturization provided by the structures and techniques defined above, it is possible to provide a physical embodiment of instrument 80 adapted to fit into a pocket. As such the dimensions should not be in excess of $3\frac{1}{4}$ inches wide, 9 inches long, and $1\frac{1}{4}$ inches deep. Furthermore, the weight of the entire unit can be restricted to approximately one-half pound. Hence, the unit is easily handled and stored. Indeed, it is possible for a doctor to slip the entire unit, when folded, as depicted in FIG. 6, into his coat pocket following patient examination. Moreover, given the provision of solar panel 89 for generation of needed power, it is not necessary for the physician, medical technician or clinician to have an electrical power outlet readily available. Alternatively, chemical batteries, etc., can be incorporated as an appropriate power source. Thus, the unit is readily adapted to use in the field, as for example, at accident scenes, etc. The RAMs incorporated in instrument 80 permit the medical technician or doctor to make a series of patient samplings which can be later recalled and inputted into a primary patient data bank.

Now turning to FIG. 7, a portable, disposable variant of cartridge 40, described above and contemplated for use with unit 80, is illustrated. Primarily, cartridge 94 includes upper portion 95 and lower portion 97 where lower portion 97 is adapted to be inserted into the complementary aperture provided in unit 80 and establish electrical contact therebetween. It is contemplated that appropriate electronic circuity and control like that described in reference to FIG. 1 is incorporated into instrument 80 to provide fluid analysis by the method described. The ROMs employed in such a unit, for example, would hold slope information for particular substances relative to the particular electrode structure.

Moving now to the particular configuration of upper portion 95, it includes a chamber containing calibrant solution and push-button calibrant injector 98 for flooding the specimen chamber (not illustrated). Further illustrated is specimen port 96 for injection of blood or other appropriate fluid into the specimen chamber. In this embodiment, it is contemplated that the waste reservoir be entirely contained within upper portion 95. The operation of this cartridge is identical to the procedures described earlier in this application.

As is readily apparent, pocket-sized unit 80 and cartridge 94 are directed to use by medical personnel, either in a hospital environment or in the field. Of course, the same principles may be employed in alternative disciplines such as environmental aquatic analysis.

Given the foregoing description of the system, the cartridge, the modified electrode structure and the single calibration referenceless technique, a host of modifications and variations thereto should now be apparent to one of ordinary skill in the art. It is intended that such modifications and variations fall within the scope of the invention as described by the appended claims.

I claim:

1. A method for calibration measurement of chemicals in a solution employing only $N+1$ sensors when $N$ is equal to the number, including one, of chemicals to be sensed, at least a first chemical species to be sensed in a solution having at least two chemicals and employing at least a first ion specific sensor and a second ion specific sensor where the first sensor is a combination electrode sensitive only to the first and a second dissimilar chemical species and the second sensor is sensitive only to the second species, the method comprising the steps of:
   (a) contacting the sensors with a solution containing at least the first and second dissimilar chemical species,
   (b) obtaining a first signal determined by the differences of the electrical charges developed by the two sensors when contacted by the solution
   (c) conveying the first signal to a signal processor,
   (d) contacting the sensors with at least a second solution containing known quantities of the first and second species and obtaining at least a second signal corresponding to the difference between the charges developed in response to the second solution by the first and second sensors,
   (e) conveying at least the second signal to a signal processor,
   (f) establishing algebraic constants from at least the second signal,
   (g) inputing the constants into a calculating device for determining the concentration of the first dissimilar chemical species.

2. A method according to claim 1 where the concentration of the first species is determined by calculations using the half cell voltage produced by the second sensor.

3. A method according to claim 2 where the voltages from the sensors are multiplexed and passed to a differential amplifier.

4. A method according to claim 1 including the steps of providing the sensors with a substantially uniform geometry at the solution interface and minimizing flux density.

5. A method according to claim 1, further comprising the step of minimizing flux density variations caused by edge effects.

6. A method according to claim 1, further including the steps of arraying the sensors along a surface of a chamber isolated from the ambient environment and introducing a precise volume of solution into the chamber.

7. A method according to claim 1 further including the step of contacting the first and second sensors with a calibrant solution containing the first and second species.

8. A method according to claim 1 where the first and second sensors are contacted by solution in vivo.

9. A method according to claim 1 further including the step of sterilizing the first and second sensors.

10. A method according to claim 1 further including the step of sterilizing the first, and second.

11. The method according to claim 1 wherein the method is practiced by sensors providing single point calibration, the method further comprising flowing N+1 solutions over the electrodes.

12. The method according to claim 1 wherein the method further comprises, establishing a uniform space charge distribution at the reactive surfaces of the sensors.

13. A method for calibration measurement of chemicals in a solution employing only N+1 sensors where N is equal to the number, including one, of chemicals to be sensed, at least a first chemical species to be sensed in a solution having at least two chemicals and employing at least a first ion specific sensor and a second ion specific sensor where the first sensor is a combination electrode sensitive only to the first and a second dissimilar chemical species and the second sensor is sensitive only to the second species, the method comprising the steps of:

(a) contacting the sensors with a solution containing at least the first and second dissimilar chemical species, (b) obtaining a first signal determined by the differences of the electrical charges developed by the two sensors when contacted by the solution (c) contacting the sensors with at least a second solution containing known quantities of the first and second species and obtaining at least a second signal corresponding to the difference between the charges developed in response to the second solution by the first and second sensors, (d) inputting said signals into signal processing means to determine the concentration of the first chemial species.

* * * * *